US00PP11783P2

(12) United States Plant Patent
Eady

(10) Patent No.: US PP11,783 P2
(45) Date of Patent: Feb. 20, 2001

(54) LAMIUM PLANT NAMED 'DELLAM'

(75) Inventor: Wayne Michael Eady, Spalding (GB)

(73) Assignee: R. Delamore Ltd., Wisbech (GB)

( * ) Notice: Under 35 U.S.C. 154(b), the term of this patent shall be extended for 0 days.

(21) Appl. No.: 09/328,639

(22) Filed: Jun. 9, 1999

(51) Int. Cl.[7] ..... A01H 5/00
(52) U.S. Cl. ..... Plt./263
(58) Field of Search ..... Plt./263

(56) References Cited

U.S. PATENT DOCUMENTS

P.P. 11,122 * 11/1999 Bovio ..... Plt./263

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Lamium plant named 'Dellam', characterized by its unique and attractive tri-colored variegated foliage; compact, freely branching and somewhat spreading growth habit; somewhat inconspicuous, but numerous lavender-colored flowers; plants typically do not scorch during the summer; and are relatively winter hardy.

1 Drawing Sheet

BACKGROUND OF THE INVENTION

The present invention relates to a new and distinct cultivar of Lamium plant, botanically known as *Lamium maculatum* and referred to by the cultivar name 'Dellam'.

The new Lamium was discovered by the Inventor as a naturally-occurring whole plant mutation of the nonpatented *Lamium maculatum* cultivar 'Gold Nuggets' in the autumn of 1997 in Wisbech, Cambridgeshire, United Kingdom. The new Lamium was selected on the basis of its unique tri-colored foliage.

Asexual reproduction of the new Lamium by terminal cuttings taken in a controlled environment in Wisbech, Cambridgeshire, United Kingdom, has shown that the unique features of this new Lamium are stable and are reproduced true to type in successive generations.

SUMMARY OF THE INVENTION

The new Lamium has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Dellam' and distinguish 'Dellam' as a new and distinct cultivar:

1. Unique and attractive tri-colored variegated foliage that is chartreuse to dull yellow at the margin, dull green interior to outer margin, and gray-green at the center.

2. Strong growing; compact, freely branching and somewhat spreading growth habit.

3 . Somewhat inconspicuous, but numerous lavender-colored flowers.

4. Plants typically do not scorch in the summer.

5. Relatively winter hardy in England.

Compared to plants of the parent, the cultivar 'Gold Nugget', plants of the new Lamium differ in foliage color and are stronger growing, resist scorching and are more winter hardy.

BRIEF DESCRIPTION OF THE PHOTOGRAPHS

The accompanying colored photographs illustrate the overall appearance of the new Lamium, showing the colors as true as it is reasonably possible to obtain in colored reproductions of this type.

The photograph at the top of the sheet comprises a top perspective view of a typical potted plant of 'Dellam'.

The photograph at the bottom of the sheet comprises close-up views of typical developing flowers and leaves of 'Dellam'. Flower and foliage colors in the photographs may appear different from the actual colors due to light reflectance.

DETAILED BOTANICAL DESCRIPTION

The following observations, measurements, values, and comparisons describe plants grown in Bonsall, Calif., under outdoor full-sun conditions with day temperatures ranging from 18 to 35° C., night temperatures ranging from 13 to 18° C. Plants were planted in 20-cm containers with three plants per container and grown for about 8 to 12 weeks. Color references are made to The Royal Horticultural Society Colour Chart except where general terms of ordinary dictionary significance are used.

Botanical classification: *Lamium maculatum* cultivar 'Dellam'.

Parentage: Naturally-occurring whole plant mutation of *Lamium maculatum* cultivar 'Gold Nuggets', not patented.

Propagation:

*Type.*—By cuttings.

*Time to initiate roots.*—Summer: About 14 days at temperatures of 21° C. Winter: About 21 days at temperatures of 18° C.

*Time to develop roots.*—About 28 days at temperatures of 18° C. during the summer.

*Root description.*—Fine and freely branching.

Plant description:

*General appearance.*—Herbaceous; low, compact and somewhat spreading plant; lavender flowers that are somewhat inconspicuous. May be annual or perennial depending on temperatures. Suitable for 12.5 to 25-cm containers and hanging baskets. To produce a finished flowering plant in a 12.5-cm container from rooted cuttings, about 8 to 12 weeks are required depending on temperature and light level.

*Plant height.*—About 12 cm.

*Plant diameter or spread.*—About 16 cm.

*Growth rate/vigor.*—Moderately vigorous.

*Stem description.*—Branching: Freely branching, typically about 8 laterals and numerous secondary laterals. Appearance: Square in cross-section. Lateral branch length: About 12.5 cm. Lateral branch diameter: About 3 mm. Internode length: About 1.5 to 2.5 cm. Texture: Pubescent. Color: 145A.

*Foliage description.*—Arrangement: Opposite, single. Quantity: About 24 per primary lateral branch; secondary laterals, about 7. Shape: Ovate to cordate. Apex: Broadly acute. Base: Cordate. Margin: Serrate to dentate. Length, lower leaves: About 3.25 cm. Width, lower leaves: About 3.75 cm. Texture: Soft; matte; fuzzy, fine hairs on both surfaces. Petiole length: About 1.5 cm. Petiole diameter: About 2 mm. Color: Young leaves, upper surface: Chartreuse at the margin, 154A; dull green, 137A, interior to outer margin, and gray-green, 148B, at the center. Young leaves, lower surface: Dull yellow, 11B, at margin, green, 147B, at center. Fully expanded leaves, upper surface: Dull yellow, 11B, at the margin, dull green, 137A, interior to outer margin, and gray-green, 148B at the center. Fully expanded leaves, lower surface: Dull yellow, 11B, at margin, green, 147B, at center. Petiole: 144D.

Flowering description:

*Flowers.*—Zygomorphic, galeate, axillary single flowers arranged in verticillasters of 5 or 6 per node. Petals fused into galeate flower form with hood-like upper lip and three-lobed lower lip. Flowers open rapidly and continue to develop rapidly lasting for only a few days. Self-cleaning. Not fragrant.

*Natural flowering season.*—Natural flowering season is spring to fall; flowering continuous during this period.

*Quantity of flowers.*—Very floriferous with typically about 26 open flowers and flower buds per lateral stem; about 200 open flowers and flower buds per plant.

*Flower height.*—About 1.5 cm.

*Flower width.*—About 9 mm.

*Flower aspect.*—Upright to nodding.

*Flower buds.*—Shape: Oblong. Length: About 6 mm. Diameter: About 3 mm. Color: Distal, 145D; proximal, 76B.

*Petals.*—Arrangement and shape: Zygomorphic and galeate; petals fused into galeate flower form with hood-like upper lip and tri-lobed lower lip. Rounded apex and entire margin. Texture: Tomentose. Color: When opening (both surfaces): Distal, 145D; proximal, 76B. Mature (both surfaces): Distal, 76A; proximal, 155D.

*Sepals.*—Quantity: Sepals fused; five-pointed, star-shaped calyx. Apex: Acute. Margin: Entire. Calyx length: About 5 mm. Calyx diameter: About 4 mm. Texture: Pubescent. Color: Upper surface, 144B; lower surface, 144A.

*Peduncle.*—Length: About 1 mm. Strength: Strong. Angle: Acute. Color: 144A.

*Androecium.*—Stamen number: Typically four per flower. Anther shape: Ovate. Anther size: About 0.1 mm. Anther texture: Pubescent. Anther color: 24A. Amount of pollen: Moderate. Pollen color: 24A.

*Gynoecium.*—Pistil number: One per flower. Stigma shape: Bifurcate. Pistil length: About 0.2 mm. Style color: 155C. Stigma color: 155C. Ovary color: 145B.

Disease resistance: Disease resistance to pathogens common to Lamium has not been observed.

Seed/fruit production: Seed and fruit production has not been observed.

It is claimed:

1. A new and distinct cultivar of Lamium plant named 'Dellam', as illustrated and described.

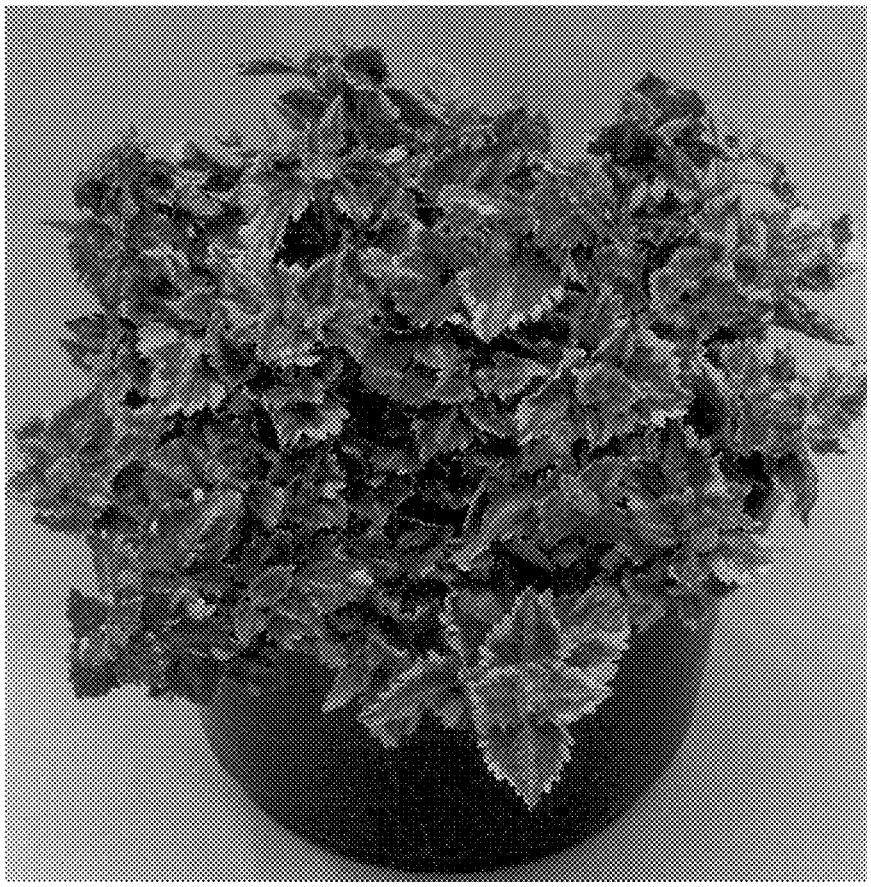
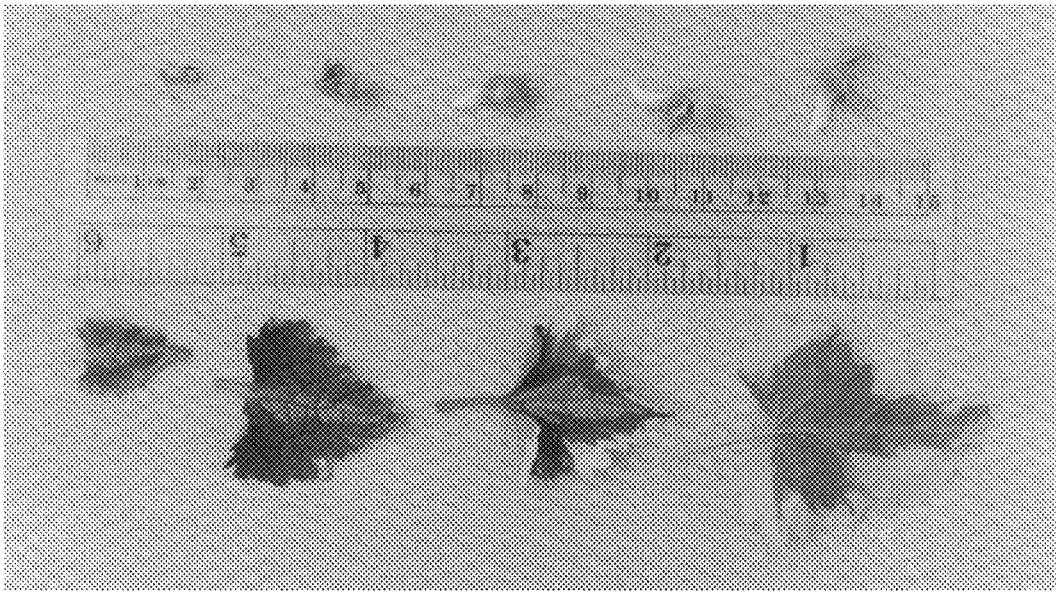

* * * * *